(12) United States Patent
Chono

(10) Patent No.: US 11,997,381 B2
(45) Date of Patent: May 28, 2024

(54) IMAGING SYSTEM, IMAGING METHOD, AND NON-TRANSITORY COMPUTER-READABLE MEDIUM

(71) Applicant: NEC Corporation, Tokyo (JP)

(72) Inventor: Keiichi Chono, Tokyo (JP)

(73) Assignee: NEC CORPORATION, Tokyo (JP)

( * ) Notice: Subject to any disclaimer, the term of this patent is extended or adjusted under 35 U.S.C. 154(b) by 107 days.

(21) Appl. No.: 17/799,727

(22) PCT Filed: Feb. 27, 2020

(86) PCT No.: PCT/JP2020/008099
§ 371 (c)(1),
(2) Date: Aug. 15, 2022

(87) PCT Pub. No.: WO2021/171501
PCT Pub. Date: Sep. 2, 2021

(65) Prior Publication Data
US 2023/0075172 A1    Mar. 9, 2023

(51) Int. Cl.
*H04N 23/667* (2023.01)
*A61B 5/1171* (2016.01)

(52) U.S. Cl.
CPC .......... *H04N 23/667* (2023.01); *A61B 5/1171* (2016.02)

(58) Field of Classification Search
CPC .................................................. H04N 23/667
See application file for complete search history.

(56) References Cited

U.S. PATENT DOCUMENTS

2002/0118864 A1    8/2002  Kondo et al.
2014/0226876 A1*   8/2014  Savvides ................ G06V 40/19
                                                    382/117
2017/0124393 A1    5/2017  Kim et al.
2017/0228594 A1*   8/2017  Takemoto ............... G06V 10/50
2019/0087657 A1    3/2019  Wang et al.

FOREIGN PATENT DOCUMENTS

| JP | H10-40386 A    | 2/1998  |
| JP | 2002-259981 A  | 9/2002  |
| JP | 2004-226729 A  | 8/2004  |
| JP | 2007-159762 A  | 6/2007  |
| JP | 2017-526997 A  | 9/2017  |
| WO | 2009/036103 A1 | 3/2009  |
| WO | 2018/187337 A1 | 10/2018 |

OTHER PUBLICATIONS

International Search Report for PCT Application No. PCT/JP2020/008099, dated May 26, 2020.
Extended European Search Report for EP Application No. 20921574.8, dated Apr. 3, 2023.

* cited by examiner

*Primary Examiner* — Mishawn N. Hunter
(74) *Attorney, Agent, or Firm* — Sughrue Mion, PLLC

(57) ABSTRACT

An imaging system (1) includes an imaging unit (2) configured to capture an eye of a target person, and a mode control unit (4) configured to select one of imaging modes including a first imaging mode that sets a capture volume for which a greatest distance from the imaging unit (2) in an optical axis direction of the imaging unit (2) is a first distance, and a second imaging mode that sets the capture volume for which the greatest distance from the imaging unit is a second distance, in which the second distance is greater than the first distance. With the imaging system (1), a balance between an image quality matching a purpose of use and a capturing time may be easily achieved.

6 Claims, 18 Drawing Sheets

IMAGING SYSTEM, IMAGING METHOD, AND NON-TRANSITORY COMPUTER-READABLE MEDIUM

This application is a National Stage Entry of PCT/JP2020/008099 filed on Feb. 27, 2020, the contents of all of which are incorporated herein by reference, in their entirety.

TECHNICAL FIELD

This disclosure relates to an imaging system, an imaging method, and a non-transitory computer-readable medium, and more particularly to an imaging system, an imaging method, and a non-transitory computer-readable medium that are used to capture an eye of a target person.

BACKGROUND ART

Biometric authentication that uses an iris of an eye (iris authentication) is known. With the biometric authentication, an iris of a target person is captured using an imaging system, and iris information is extracted. The imaging system includes a plurality of imaging modes matching purposes of use. For example, in a registration mode, the imaging system adds the iris information that is extracted to a database, and registers the target person. In an authentication mode, the imaging system checks the iris information that is extracted against the iris information that is registered in the database, and authenticates the target person. With such an imaging system, image quality that is demanded is different depending on the purpose of use, and there is a demand to reduce a capturing time while guaranteeing an image quality.

Patent Literature 1 discloses an imaging system for guiding an object based on a distance to the object, and for capturing a region including an eye of the object.

Patent Literature 2 discloses an imaging system for reducing a capturing time depending on a purpose of use, by switching a focal point control method according to a type of imaging mode.

CITATION LIST

Patent Literature

Patent Literature 1: Japanese Unexamined Patent Application Publication No. 2007-159762
Patent Literature 2: Japanese Unexamined Patent Application Publication No. 2004-226729

SUMMARY OF INVENTION

Technical Problem

This disclosure is for improving the related art described above.

Solution to Problem

An imaging system according to a first aspect of the disclosure includes:
  an imaging unit configured to capture an eye of a target person; and
  a mode control unit configured to select one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance,
  in which the second distance is greater than the first distance.

An imaging method according to a second aspect of the disclosure includes:
  a step of capturing an eye of a target person by an imaging unit; and
  a step of selecting, by a mode control unit, one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance,
  in which the second distance is greater than the first distance.

A non-transitory computer-readable medium according to a third aspect of the disclosure stores an imaging program for causing a computer to implement:
  an imaging function of causing an imaging unit to perform a process of capturing an eye of a target person; and
  a mode control function of selecting one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance, the second distance being greater than the first distance.

EXAMPLE EMBODIMENT

Figure 1:
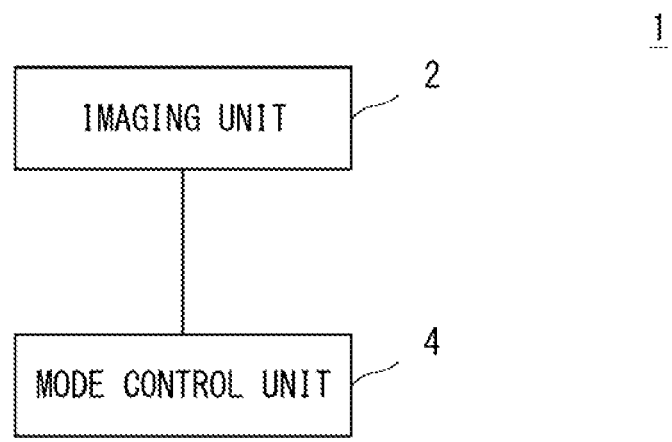
FIG. 1 is a block diagram showing a configuration of an imaging system according to an outline of a first example embodiment.

Hereinafter, specific example embodiments will be described in detail with reference to the drawings. In the drawings, same or corresponding elements are denoted by a same reference sign, and overlapping description are omitted as necessary for the sake of clarity.

FIRST EXAMPLE EMBODIMENT

FIG. 1 is a block diagram showing a configuration of an imaging system 1 according to a first example embodiment. The imaging system 1 includes an imaging unit 2 and a mode control unit 4.

The imaging unit 2 is for capturing an eye of a target person.

The mode control unit 4 selects one of imaging modes. The imaging modes include a first imaging mode that sets a capture volume for which a greatest distance from the imaging unit 2 in an optical axis direction of the imaging unit 2 is a first distance, and a second imaging mode that sets a capture volume for which the greatest distance from the imaging unit 2 is a second distance. The second distance is greater than the first distance.

According to Patent Literature 1 described above, capturing is performed by guiding an object to a predetermined position regardless of the imaging mode, and there is a problem that capturing matching the purpose of use cannot be performed.

Furthermore, according to Patent Literature 2 described above, the imaging system has to include a plurality of focal point control methods, and there is a problem that a structure is complex.

However, according to the configuration of the first example embodiment, the imaging system 1 changes the capture volume, or more particularly, the greatest distance from the imaging unit 2, according to the imaging mode. Accordingly, in the case of an imaging mode corresponding to a purpose of use requiring a high image quality, an image of a higher image quality may be acquired by reducing the distance. Furthermore, in the case of an imaging mode corresponding to a purpose of use requiring a relatively low image quality, adjustment of a position of a target person P may be omitted or a time for adjustment may be reduced by increasing the distance, and a capturing time may thus be reduced. In this manner, with the imaging system 1, a balance may be easily achieved between the image quality matching the purpose of use and the capturing time. Furthermore, a space may be saved because one imaging unit 2 performs imaging in a plurality of imaging modes.

SECOND EXAMPLE EMBODIMENT

In the following, a second example embodiment of the disclosure will be described with reference to FIGS. 2 to 4.

Figure 2:
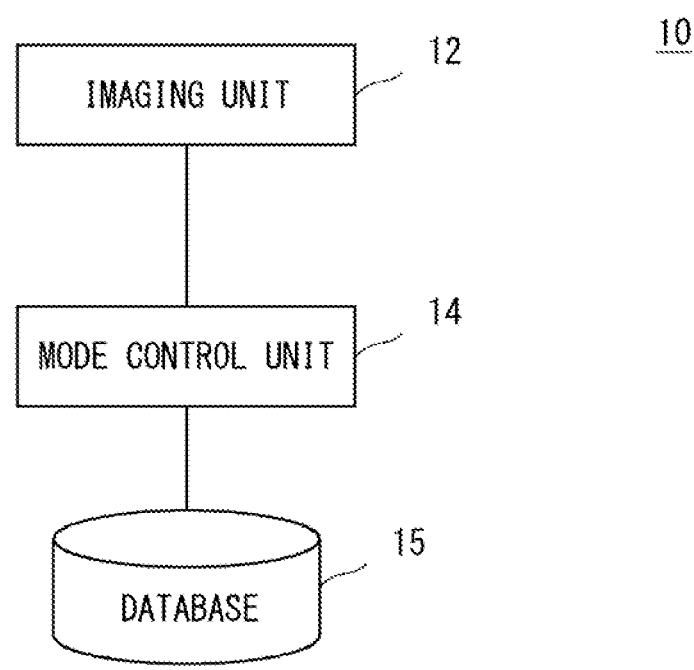
FIG. 2 is a block diagram showing a configuration of an imaging system according to a second example embodiment.
Figure 3:
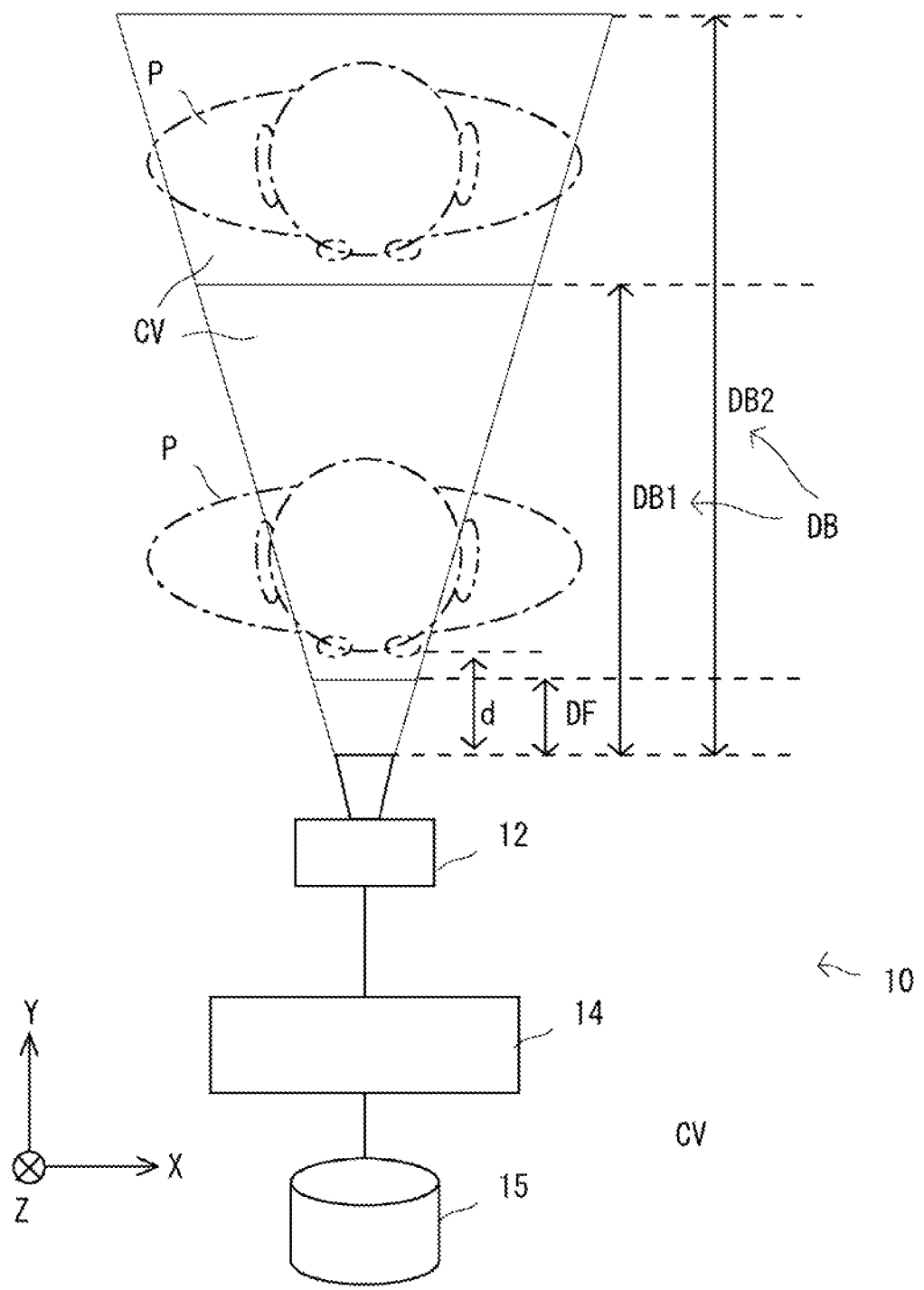
FIG. 3 is a schematic configuration diagram of the imaging system according to the second example embodiment.

FIG. 2 is a block diagram showing a configuration of an imaging system 10. The imaging system 10 is a computer or the like that performs biometric authentication, and the imaging system 10 captures a focused region including an eye of the target person P, extracts biometric authentication information included in the image that is captured, and performs a process according to the purpose of use. In the second example embodiment, the biometric authentication is iris authentication. The imaging system 10 includes an imaging unit 12, a mode control unit 14, and a database 15.

Details of various components of the imaging system 10 will be described with reference to FIG. 3. FIG. 3 is a schematic configuration diagram of the imaging system 10 according to the second example embodiment.

Additionally, in the present drawing, an optical axis direction of the imaging unit 12 of the imaging system 10 described later will be given as a Y-axis direction, a height direction of the target person P as a Z-axis direction, and a direction perpendicular to the Y-axis and Z-axis directions as an X-axis direction. Furthermore, for the sake of convenience, a direction on an X-Y plane will be given as a horizontal direction, and the Z-axis direction as a vertical direction.

Furthermore, in the second example embodiment, a distance between an imaging surface of the imaging unit 12 described later and a face of the target person P will be referred to as an object distance d.

The imaging unit 12 of the imaging system 10 is a camera for capturing an eye, especially an iris, of the target person P. The imaging unit 12 includes an image sensor such as a charge coupled device (CCD) or a complementary metal oxide semiconductor (CMOS). The imaging surface of the imaging unit 12 includes a pixel array where photoelectric conversion units, not shown, for converting an optical image of the target person P into electric signals are two-dimensionally arranged. The imaging surface of the imaging unit 12 is installed parallel to the X-axis direction, with a normal direction in parallel to the Y-axis direction.

In the second example embodiment, the imaging unit 12 may be a general-purpose camera with 12M pixels (4000 pixels horizontally, 3000 pixels vertically) and 60 fps, which is becoming popular as an industrial camera or the like.

The imaging unit 12 is installed such that the focused region including an eye of the target person P positioned inside a capture volume CV can be desirably captured. The capture volume CV is a region where an imaging target can be normally captured at a level usable for biometric authentication. The capture volume CV in the horizontal direction in the second example embodiment is a region defined by a horizontal angle of view of the imaging unit 12, a forward most distance DF and a rearward most distance DB.

The forward most distance DF is a distance closest to the imaging unit 12 in the optical axis direction of the imaging unit 12 (that is, the Y-axis direction), in the capture volume CV in the horizontal direction. In the second example embodiment, the forward most distance DF may be an object distance at which a field of view of the imaging unit 12 covers both eyes of one target person P.

The rearward most distance DB is a farthest distance from the imaging unit 12 in the Y-axis direction, in the capture volume CV in the horizontal direction.

The imaging unit 12 captures the target person P according to a control signal output from the mode control unit 14.

The mode control unit 14 selects one of the imaging modes, and controls an imaging operation of the imaging unit 12 according to the imaging mode. The imaging modes include the first imaging mode and the second imaging mode. Different capture volumes CV are set for the first and second imaging modes.

As shown in the present drawing, a capture volume CV where the rearward most distance DB is a first distance (DB1) is set in the first imaging mode. The first imaging mode in the second example embodiment may be a registration mode for registering the target person P.

Furthermore, as shown in the present drawing, a capture volume CV where the rearward most distance DB is a second distance (DB2) is set in the second imaging mode. The second distance (DB2) is greater than the first distance (DB1). In the second example embodiment, the second imaging mode may be an authentication mode for authenticating the target person P.

Furthermore, the mode control unit 14 performs a feature extraction process for extracting iris information (in the second example embodiment, a feature of the iris) from an iris pattern that is acquired. The mode control unit 14 is connected to the database 15, and inputs/outputs various pieces of information from the database 15 according to the imaging mode.

For example, in the case where the imaging mode is the first imaging mode (the registration mode), new iris information is registered in the database 15.

In the case where the imaging mode is the second imaging mode (the authentication mode), the mode control unit 14 checks the iris information that is acquired against the iris information that is registered in the database 15 to authenticate the target person P.

The database 15 is a storage medium for storing various pieces of information such as iris information.

Additionally, in the second example embodiment, the database 15 is included in the imaging system 10, but this is not restrictive. The database 15 may be included in another apparatus (not shown) that is communicably connected. In this case, the imaging system 10 may include an unspecified type of communication means (not shown), and the mode control unit 14 may perform transmission/reception of various pieces of information with the other apparatus via the communication means.

Figure 4:
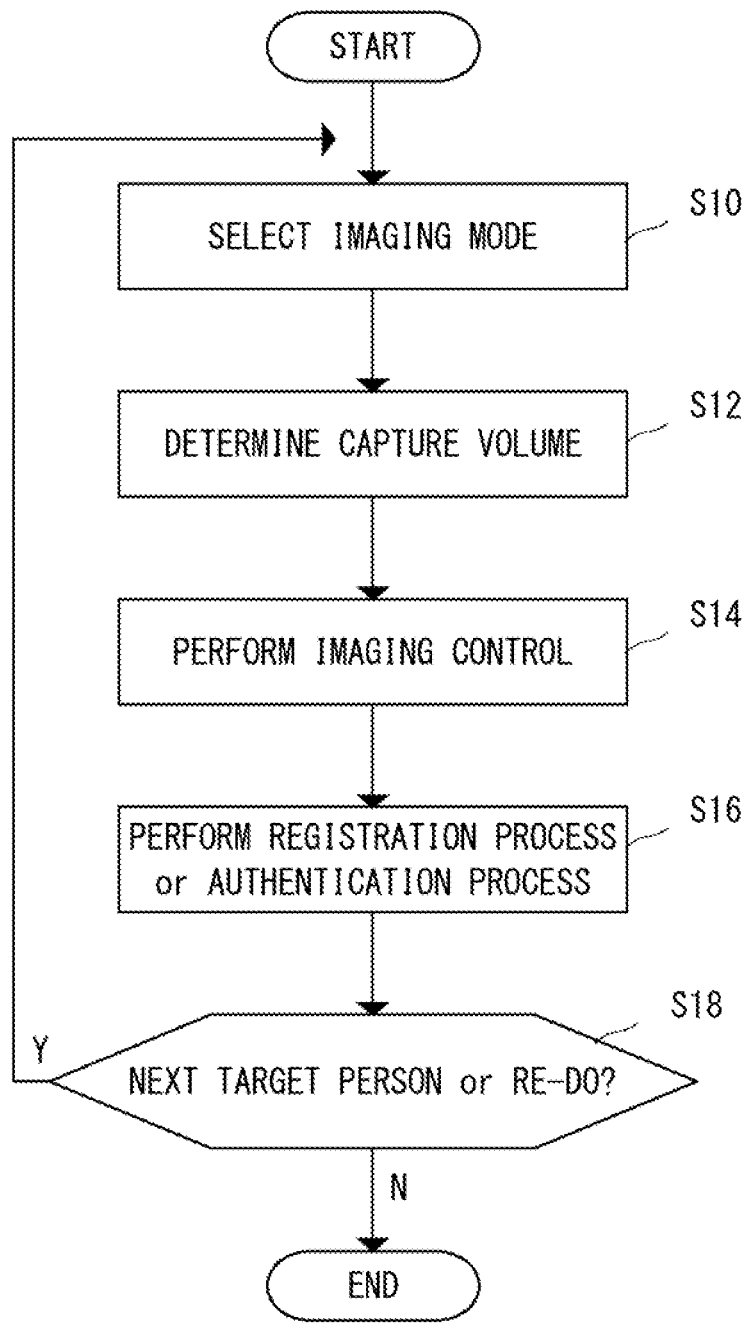
FIG. 4 is a flowchart showing a process by the imaging system according to the second example embodiment.

FIG. 4 is a flowchart showing a process by the imaging system 10 according to the second example embodiment.

First, in S10, the mode control unit 14 selects an imaging mode. At this time, the mode control unit 14 may select the imaging mode in response to reception of input from a user through input means (not shown) of the imaging system 10.

Next, in S12, the mode control unit 14 determines the capture volume CV according to the imaging mode that is selected. For example, in the case where the first imaging mode is selected, the mode control unit 14 determines the rearward most distance DB of the capture volume CV as the first distance DB1, and in the case where the second imaging mode is selected, the rearward most distance DB of the capture volume CV is determined as the second distance DB2.

Next, in S14, the mode control unit 14 controls the imaging unit 12, and causes the imaging unit 12 to perform an operation of capturing an eye of the target person P. In the second example embodiment, the imaging unit 12 captures both eyes of the target person P. Then, the mode control unit 14 acquires a captured image of irises of the target person P.

Next, in S16, the mode control unit 14 extracts a feature from the pattern of the irises of the eyes of the target person P that are captured, by using the captured image of the irises that is acquired, and performs a process according to the imaging mode (the registration process or the authentication process). That is, in the case where the imaging mode is the first imaging mode (the registration mode), the feature that is extracted is registered in the database 15 as new iris information. In the case where the imaging mode is the second imaging mode (the authentication mode), the mode control unit 14 checks the feature that is extracted against a feature that is registered in the database 15, and determines match/non-match based on a check score.

Next, in S18, the mode control unit 14 determines whether there is a next target person P, or whether to perform re-authentication or re-registration. In the case where it is determined that there is a next target person P, or that re-authentication or re-registration is to be performed (Y in S18), the mode control unit 14 returns the process to S10; in other case (N in S18), the process is ended.

In this manner, according to the second example embodiment, the imaging system 10 changes the capture volume CV, especially the rearward most distance DB, according to the imaging mode. Accordingly, in the first imaging mode (the registration mode) corresponding to a purpose of use requiring a high image quality, an image of a higher image quality may be acquired by reducing the rearward most distance DB. Furthermore, in the second imaging mode (the authentication mode) corresponding to a purpose of use requiring a relatively low image quality, by increasing the rearward most distance DB, adjustment of the object distance d may be omitted or an adjustment time may be reduced, and the capturing time may thus be reduced. In this manner, with the imaging system 10, a balance between an image quality matching the purpose of use and the capturing time may be more easily achieved. Moreover, because one imaging unit 12 performs imaging in a plurality of imaging modes, a space may be saved.

Additionally, in the second example embodiment, the imaging system 10 captures both eyes of the target person P, but instead, it is also possible to perform capturing of one eye. In this case, the forward most distance DF may be an object distance at which the field of view of the imaging unit 12 covers one eye of one target person P.

THIRD EXAMPLE EMBODIMENT

Figure 5:
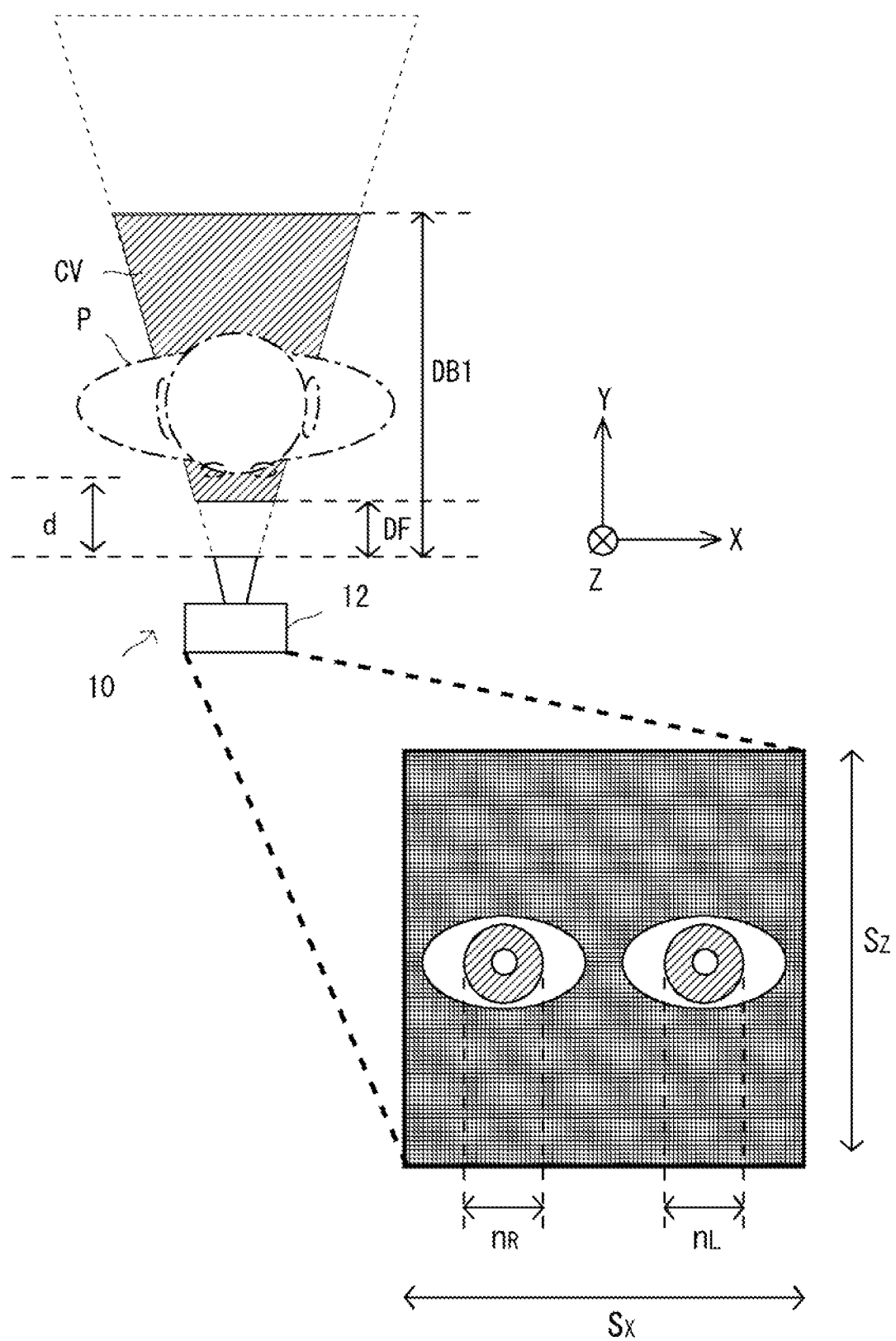
FIG. 5 is a diagram for describing a capture volume in a first imaging mode of an imaging system according to a third example embodiment.

Next, a third example embodiment of the disclosure will be described with reference to FIGS. 5 and 6. Additionally, the imaging system 10 according to the third example embodiment is the same as the imaging system 10 according to the second example embodiment, and description thereof will be omitted. FIG. 5 is a diagram for describing the capture volume CV in the first imaging mode (the registration mode) of the imaging system 10 according to the third example embodiment.

Here, resolution of the imaging unit 12 is given as $S_X \times S_Z$, and the number of pixels in the X-axis direction included in the irises of both eyes of the target person P imaged on the pixel array on the imaging surface, or in other words, the number of pixels, in a captured image, in the X-axis direction included in the irises of both eyes of the target person P positioned at the object distance d, is given as n. The number of pixels n is dependent on the resolution of the imaging unit 12, a pixel size, a focal length of a lens of the imaging unit 12, and the object distance d. In the third example embodiment, the imaging system 10 does not have to change the resolution of the imaging unit 12, the pixel size, and the focal length of the lens of the imaging unit 12, regardless of the imaging mode. Accordingly, the number of pixels n is substantially dependent on the object distance d.

Now, in the present drawing, the numbers of pixels in the X-axis direction included in the irises of a right eye and a left eye are given as $n_R$ and $n_L$, and n is a total of $n_R$ and $n_L$. Furthermore, the number of pixels in the X-axis direction required in the first imaging mode to be included in the irises of both eyes, is given as N1. Additionally, $S_X$, $S_Z$, n, $n_R$, $n_L$, and N1 are each a natural number.

The capture volume CV in the first imaging mode (the registration mode) is a region indicated by diagonal lines in the present drawing.

As shown in the present drawing, in the case where the target person P is positioned within the capture volume CV in the first imaging mode, the object distance d is equal to or greater than the forward most distance DF, and equal to or smaller than the first distance DB1.

The forward most distance DF is a smallest value of the object distance d in the case where the entire irises of both eyes of the target person P are imaged within the pixel array on the imaging surface, or in other words, in the case where the entire irises of both eyes of the target person P are contained in the image that is captured.

The first distance DB1 as the rearward most distance DB is the object distance d greater than the forward most distance DF, where a difference between the number of pixels n and the number of pixels N1 is smallest (however, n<N1).

Figure 6:
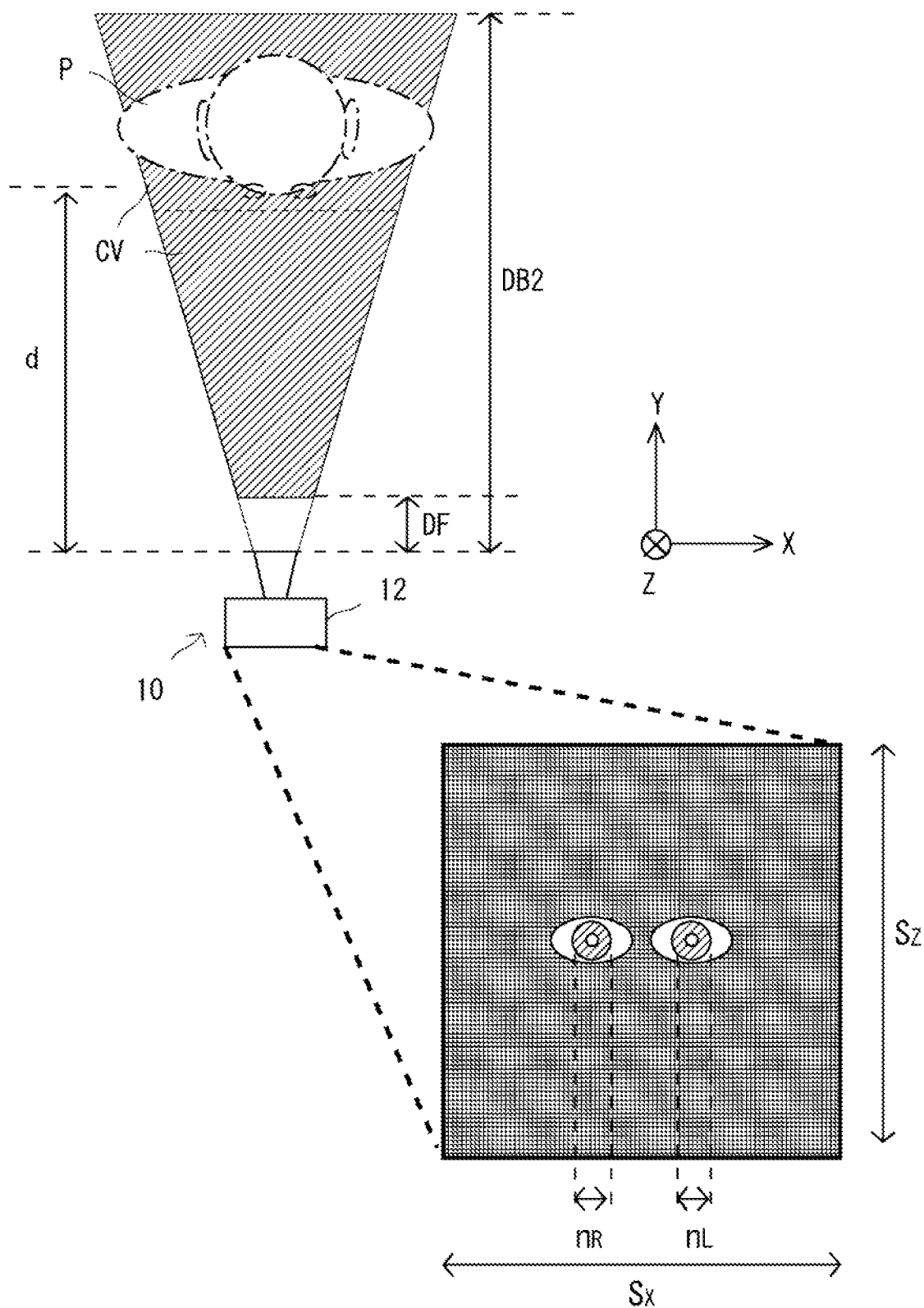
FIG. 6 is a diagram for describing the capture volume in a second imaging mode of the imaging system according to the third example embodiment.

FIG. 6 is a diagram for describing the capture volume CV in the second imaging mode of the imaging system 10 according to the third example embodiment.

The number of pixels in the X-axis direction required in the second imaging mode to be included in the irises of both eyes is given as N2. Additionally, N2 is a natural number.

The capture volume CV in the second imaging mode (the authentication mode) is a region indicated by diagonal lines in the present drawing.

As shown in the present drawing, in the case where the target person P is positioned within the capture volume CV in the second imaging mode, the object distance d is equal to or greater than the forward most distance DF, and equal to or smaller than the second distance DB2. The forward most distance DF in the second imaging mode may be the same as the forward most distance DF in the first imaging mode.

The second distance DB2 is the object distance d greater than the forward most distance DF, where a difference between the number of pixels n and the number of pixels N2 is smallest (however, n<N2).

Generally, the image quality required in the authentication mode may be lower than the image quality required in the registration mode. That is, the number of pixels N2 may be smaller than the number of pixels N1. Accordingly, the number of pixels n included in both eyes captured in the first imaging mode may be greater than the number of pixels n included in both eyes captured in the second imaging mode.

Additionally, the numbers of pixels n, N1, and N2 may be numbers of pixels in an area (X-Z plane), instead of being the numbers of pixels along a line (the X-axis direction).

Additionally, in the third example embodiment, the imaging system 10 captures both eyes of the target person P, but instead, it is also possible to perform capturing of one eye. In this case, the forward most distance DF may take a smallest value of the object distance d where the iris of the right eye (or the left eye) of the target person P that is imaged is contained within the pixel array on the imaging surface. The numbers of pixels N1 and N2 may each be the number of pixels in the X-axis direction required in the first or second imaging mode to be included in the iris of the right eye (or the left eye). Furthermore, the first distance DB1 and the second distance DB2 may be defined using the number of pixels $n_R$ or $n_L$, instead of the number of pixels n.

FOURTH EXAMPLE EMBODIMENT

Next, a fourth example embodiment of the disclosure will be described with reference to FIGS. 7 to 9. The fourth example embodiment is characterized in that an imaging system 20 includes a guide unit for guiding the target person P to a position. The imaging system 20 is a computer or the like that performs biometric authentication, especially iris authentication, and the imaging system 20 captures the focused region including an eye of the target person P, extracts biometric authentication information included in the image that is captured, and performs a process according to the purpose of use.

Figure 7:
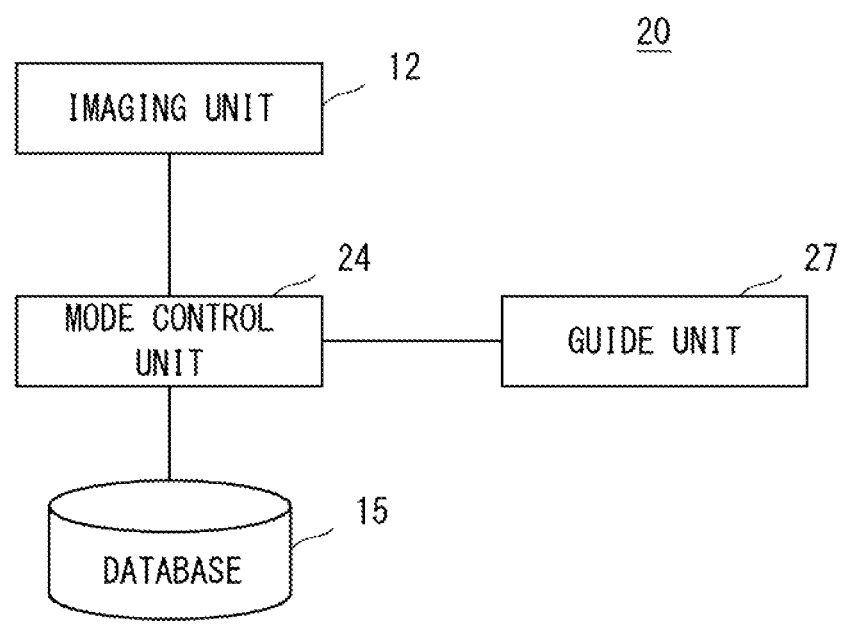
FIG. 7 is a block diagram showing a configuration of an imaging system according to a fourth example embodiment.
Figure 8:
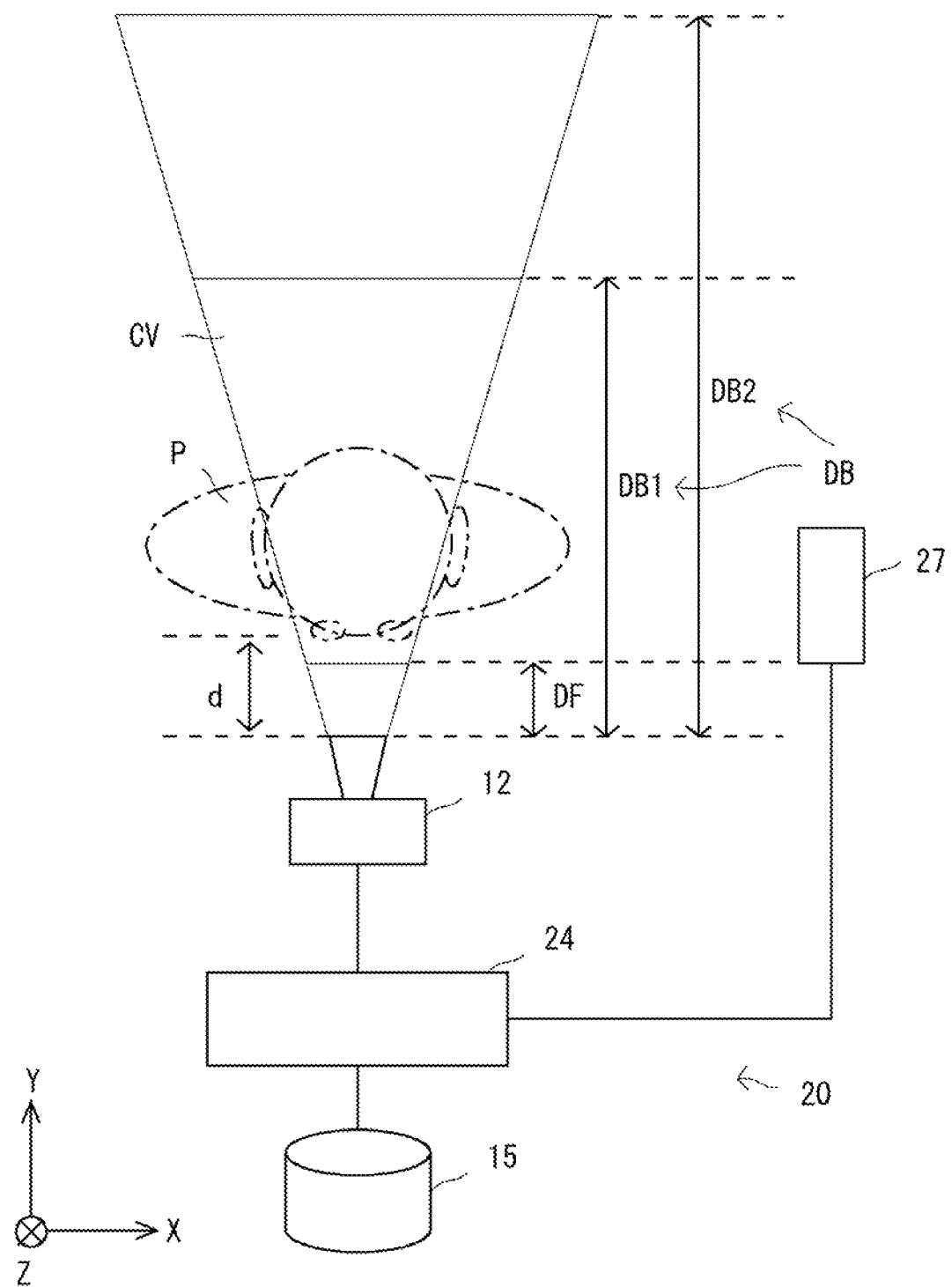
FIG. 8 is a schematic configuration diagram of the imaging system according to the fourth example embodiment.

FIG. 7 is a block diagram showing a configuration of the imaging system 20 according to the fourth example embodiment. The imaging system 20 has structure and functions that are basically the same as those of the imaging system 10 of the second example embodiment. However, the imaging system 20 is different from the imaging system 10 in that a mode control unit 24 and a guide unit 27 are included instead of the mode control unit 14.

The imaging system 20 will be described in detail with reference to FIG. 8, in relation to the differences. FIG. 8 is a schematic configuration diagram of the imaging system 20 according to the fourth example embodiment.

The guide unit 27 guides the target person P into the capture volume CV corresponding to the imaging mode that is selected. The guide unit 27 may include a display apparatus such as a display, a projection apparatus such as a projector, an audio output apparatus, or any other output apparatuses.

The mode control unit 24 has structure and functions that are basically the same as those of the mode control unit 14, and in addition, performs control of a guide operation by the guide unit 27.

Figure 9:
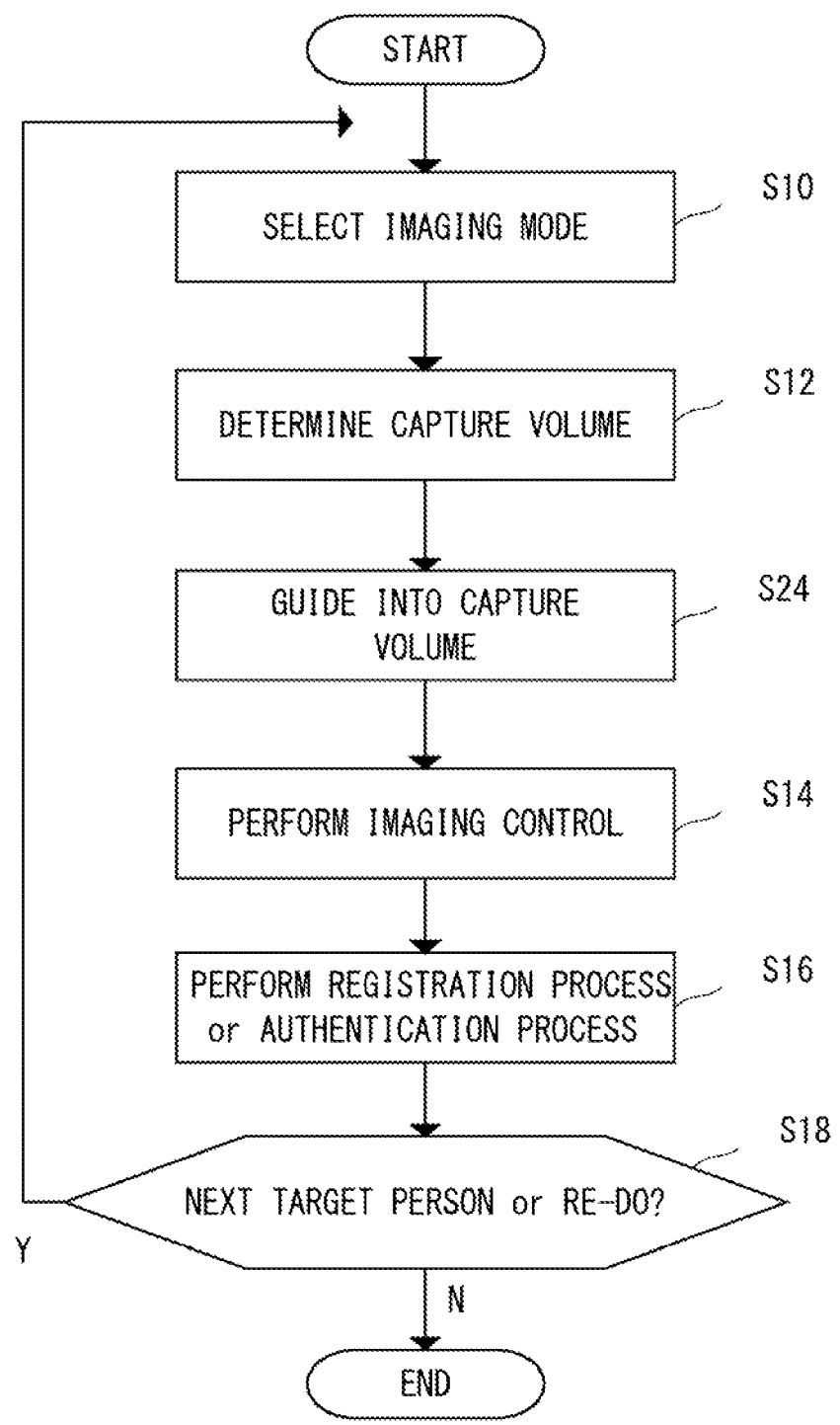
FIG. 9 is a flowchart showing a process by the imaging system according to the fourth example embodiment.

FIG. 9 is a flowchart showing a process by the imaging system 20 according to the fourth example embodiment. Steps shown in FIG. 9 include S24 in addition to the steps, shown in FIG. 4, by the imaging system 10 according to the second example embodiment. Additionally, steps the same as the steps shown in FIG. 4 will be denoted by same reference signs, and description thereof will be omitted.

In S24, in response to determination of the capture volume CV by the mode control unit 14 in S12, the guide unit 27 guides the target person P into the capture volume CV corresponding to the imaging mode, by being controlled by the mode control unit 14. Then, the mode control unit 14 performs the process in S14.

In this manner, according to the fourth example embodiment, the guide unit 27 of the imaging system 20 guides the target person P into the capture volume CV corresponding to the imaging mode, and thus, the target person P may be appropriately moved to a position according to the imaging mode. Furthermore, with the imaging system 20, the capture volume CV is different depending on the imaging mode, and thus movement of the target person P may be omitted or reduced depending on the purpose of use. Accordingly, a balance between a quality of a captured image matching the purpose of use and the capturing time may be more easily achieved.

Additionally, in the fourth example embodiment, the guide unit 27 guides the target person P into the capture volume CV corresponding to the image mode in response to determination of the capture volume CV by the mode control unit 24 in S12. However, instead, the mode control unit 24 may determine, based on the object distance d, whether the target person P is positioned within the capture volume CV corresponding to the imaging mode, in response to determination of the capture volume CV by the mode control unit 24 in S12.

For example, in the case of the first imaging mode (the registration mode), the mode control unit 24 may determine that the target person P is positioned within the capture volume CV corresponding to the imaging mode, when the object distance d is equal to or greater than the forward most distance DF and equal to or smaller than the first distance DB1. Additionally, in the case of the second imaging mode (the authentication mode), the first distance DB1 is read as the second distance DB2.

In the case of determining that the target person P is positioned within the capture volume CV, the mode control unit 24 may perform the process in S14, and in other case, the mode control unit 24 may perform the process in S24.

In this case, the imaging system 20 may include a distance measuring unit (not shown) that includes a distance measuring sensor for measuring the object distance d by being controlled by the mode control unit 24, and that outputs a measurement result to the mode control unit 24.

The guide unit 27 thus guides the target person P when the target person P is not positioned within the capture volume CV, and excessive guiding may be avoided, and the capturing time may be reduced.

FIFTH EXAMPLE EMBODIMENT

Figure 10:
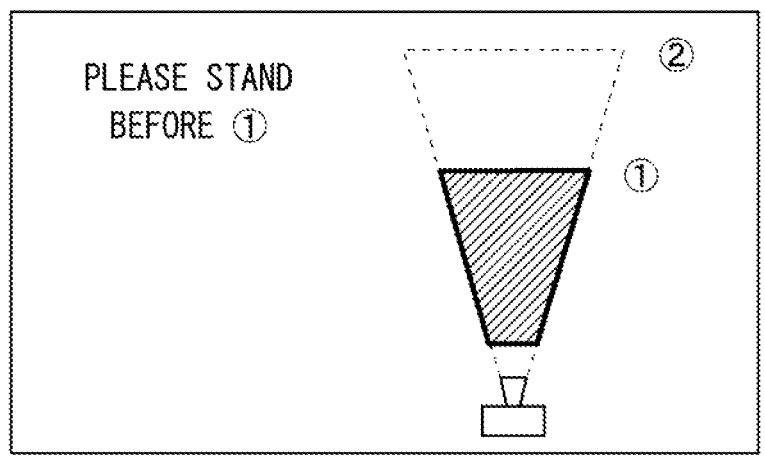
FIG. 10 is a diagram for describing an example of a guide display by an imaging system according to a fifth example embodiment.
Figure 11:
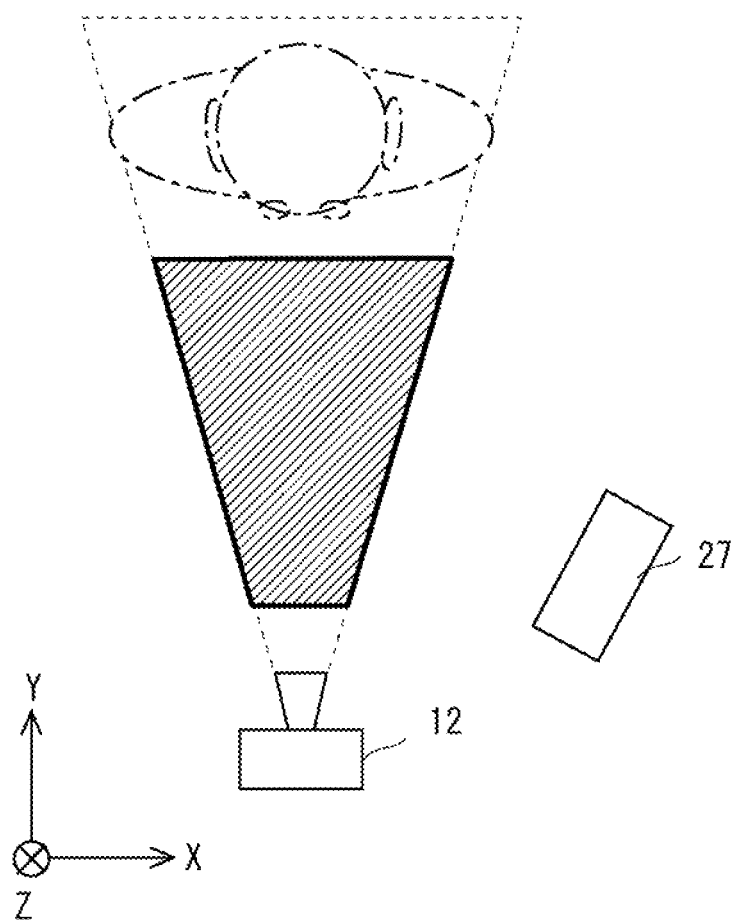
FIG. 11 is a diagram for describing an example of the guide display by the imaging system according to the fifth example embodiment.
Figure 12:
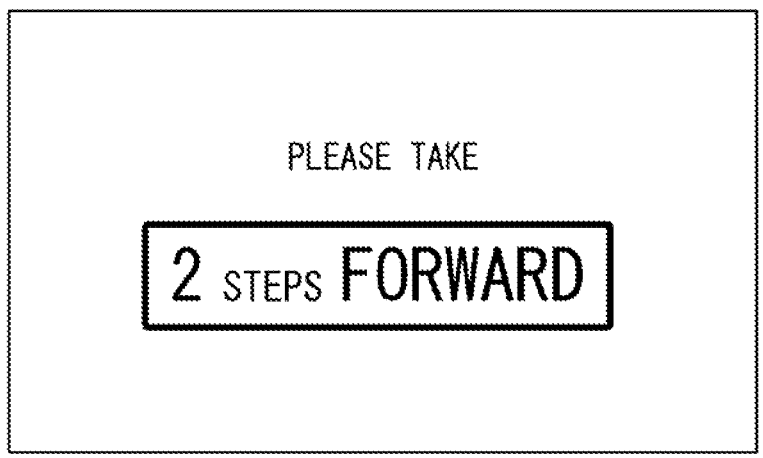
FIG. 12 is a diagram for describing an example of the guide display by the imaging system according to the fifth example embodiment.

Next, a fifth example embodiment of the disclosure will be described with reference to FIGS. 10 to 12. Additionally, the imaging system 20 according to the fifth example embodiment is the same as the imaging system 20 according to the fourth example embodiment, and description thereof will be omitted. The guide unit 27 of the imaging system 20 of the fifth example embodiment guides the target person P into the capture volume CV through various displays. FIGS. 10 to 12 are diagrams for describing examples of guide display by the imaging system 20 according to the fifth example embodiment.

FIG. 10 is an example of a case where the guide unit 27 of the imaging system 20 displays a position of the capture volume CV on a display. For example, it is assumed that a plurality of marks indicating positions of the capture volume CV corresponding to the imaging modes are installed in advance on a floor or the like near the imaging unit 12. For example, when an imaging mode is selected, the guide unit 27 may display, on the display, which mark is the mark corresponding to the imaging mode, and may encourage the target person P to move to the capture volume CV. The guide unit 27 may also visually display, on the display, the position of the capture volume CV. The target person P may thereby easily grasp a standing position for capturing.

FIG. 11 shows an example of a case where the guide unit 27 of the imaging system 20 projects the position of the capture volume CV on the floor or the like. For example, when an imaging mode is selected, the guide unit 27 may project the position of the capture volume CV corresponding to the imaging mode by using a projection apparatus such as a projector. The target person P may thereby easily grasp the standing position for capturing.

FIG. 12 shows an example of a case where the guide unit 27 of the imaging system 20 informs the target person P of the number of steps or the distance required in relation to movement. In this case, the imaging system 20 includes a distance measuring unit (not shown) that includes a distance measuring sensor for measuring the object distance d by being controlled by the mode control unit 24. The mode control unit 24 calculates the number of steps or the distance required for the target person P to move, based on the object distance d that is measured and the capture volume CV corresponding to the imaging mode that is selected. Then, the guide unit 27 displays, on the display, the number of steps or the distance that is calculated, by being controlled by the mode control unit 24, and encourages the target person P to move. The target person P may thereby easily move to an appropriate standing position.

Additionally, in the fifth example embodiment, an example where the guide unit 27 visually guides the target person P using the display, the projection apparatus or the like is described, but instead or in addition, the guide unit 27 may guide the target person P by using audio or another output method.

SIXTH EXAMPLE EMBODIMENT

Next, a sixth example embodiment of the disclosure will be described with reference to FIGS. 13 to 15. The sixth example embodiment is characterized in that an imaging system 30 selects the imaging mode based on a captured image of the entire target person P.

Figure 13:
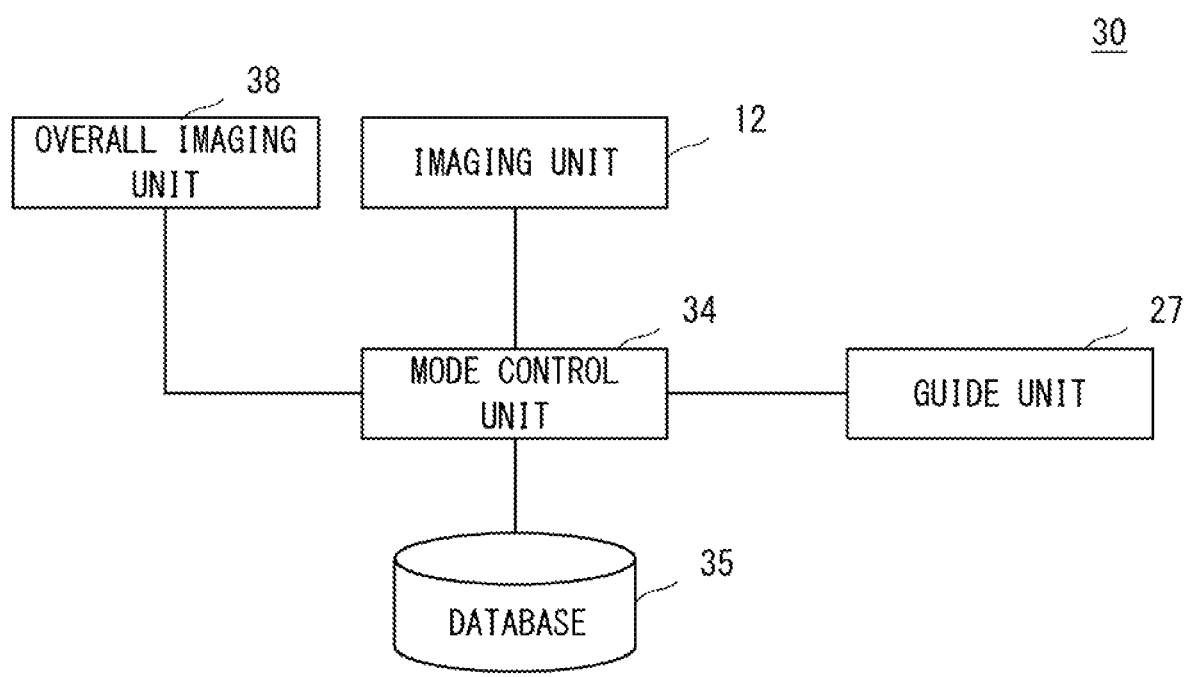
FIG. 13 is a block diagram showing a configuration of an imaging system according to a sixth example embodiment.
Figure 14:
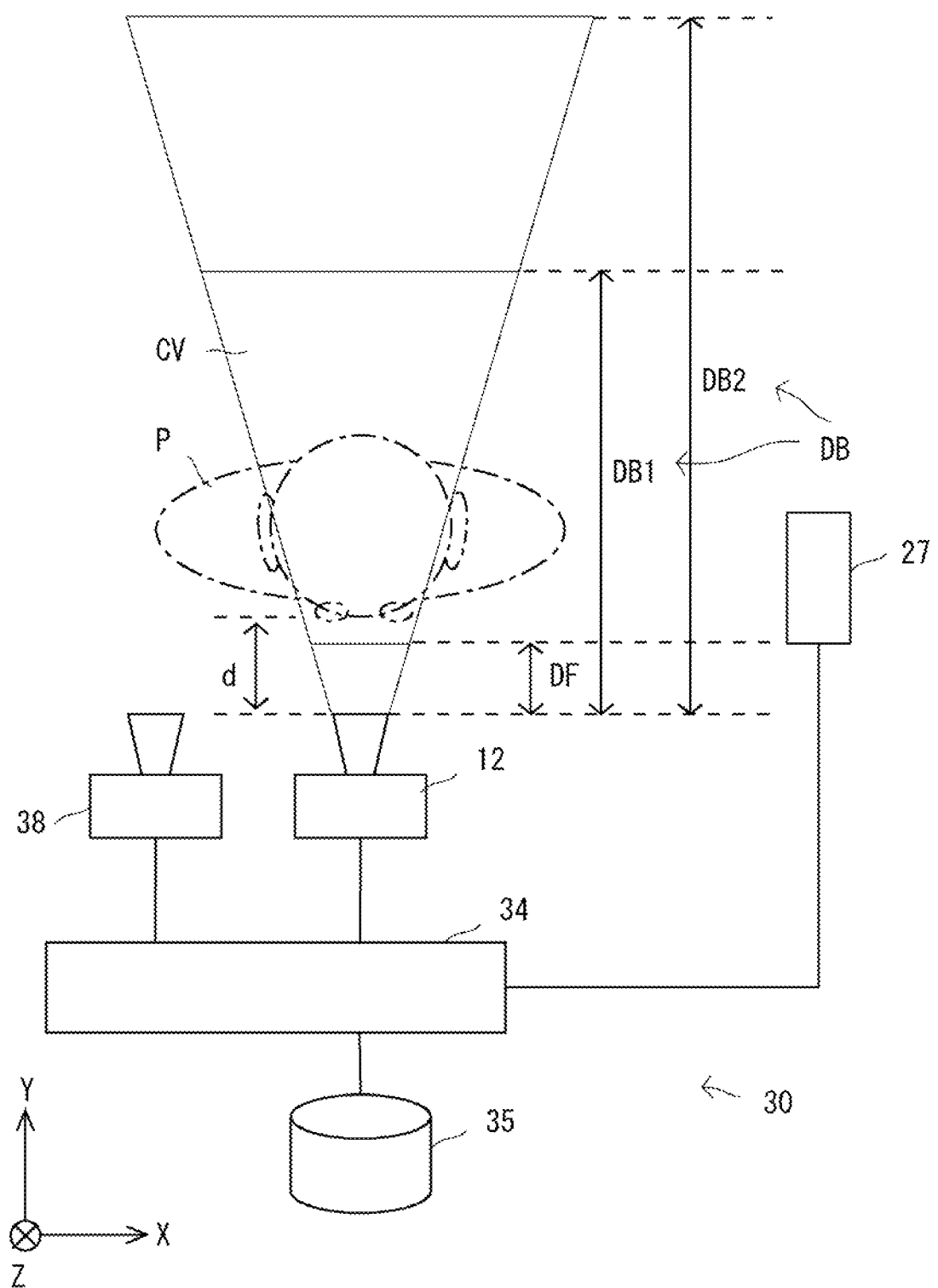
FIG. 14 is a schematic configuration diagram of the imaging system according to the sixth example embodiment.

FIG. 13 is a block diagram showing a configuration of the imaging system 30 according to the sixth example embodiment. The imaging system 30 is a computer or the like that performs biometric authentication, especially iris authentication, and the imaging system 30 captures the focused region including an eye of the target person P, extracts biometric authentication information included in the image that is captured, and performs a process according to the purpose of use. The imaging system 30 has structure and functions that are basically the same as those of the imaging system 20 of the fourth example embodiment. However, the imaging system 30 is different from the imaging system 20 in that a mode control unit 34, a database 35, and an overall imaging unit 38 are included instead of the mode control unit 24 and the database 15.

Details of the differences will be described with reference to FIG. 14. FIG. 14 is a schematic configuration diagram of the imaging system 30 according to the sixth example embodiment.

The overall imaging unit 38 is a camera for capturing the entire target person P. The overall imaging unit 38 captures the target person P using a range of field of view wider than the range of field of view of the imaging unit 12 such that tall and short persons may be covered. In the sixth example embodiment, the overall imaging unit 38 has a resolution that is enough to enable authentication of the target person P by the face. The overall imaging unit 38 captures the face of the target person P according to a control signal output from the mode control unit 34.

The mode control unit 34 has structure and functions that are basically the same as those of the mode control unit 24, and in addition, performs control of overall capturing operation of the overall imaging unit 38, and face registration and face authentication processes. Furthermore, the mode control unit 34 determines the imaging mode based on an image from the overall imaging unit 38. Additionally, the mode control unit 34 performs input/output of various pieces of information from the database 35 instead of the database 15.

The database 35 is a storage medium that has structure and functions that are basically the same as those of the database 15, and in addition, the database 35 stores various pieces of information that are used in the face authentication process, such as a feature of the face of the target person P.

Figure 15:
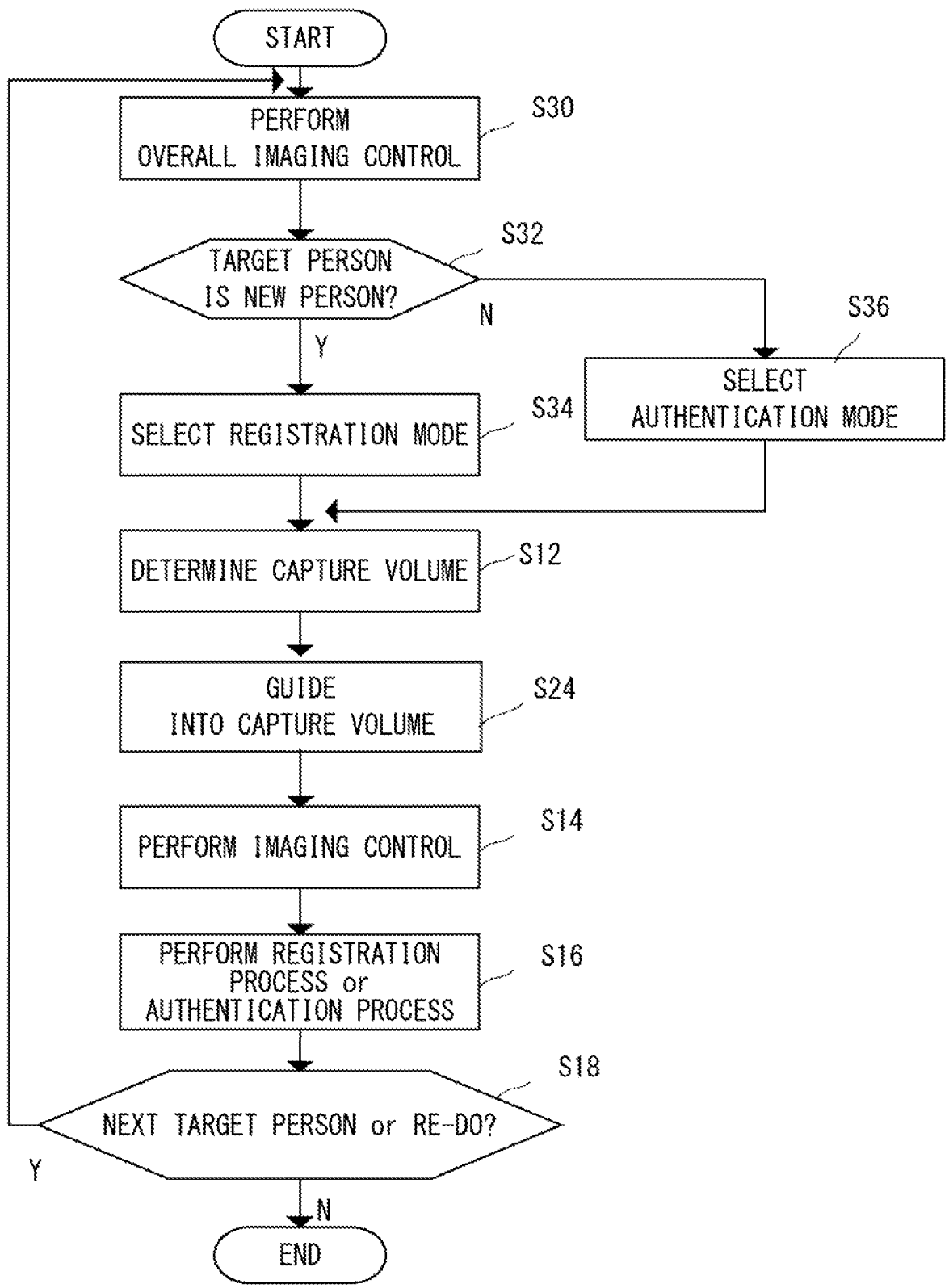
FIG. 15 is a flowchart showing a process by the imaging system according to the sixth example embodiment.

FIG. 15 is a flowchart showing a process by the imaging system 30 according to the sixth example embodiment. Steps shown in FIG. 15 include S30 to S36 instead of S10, shown in FIG. 9, by the imaging system 20 according to the fourth example embodiment. Additionally, steps same as the steps shown in FIG. 9 will be denoted by same reference signs, and description thereof will be omitted.

First, in S30, the mode control unit 34 controls the overall imaging unit 38, and cause the overall imaging unit 38 to perform an operation of capturing the face of the target person P. Then, the mode control unit 14 acquires a captured image of the face of the target person P.

Next, in S32, the mode control unit 34 determines whether the target person P is a new person. At this time, the mode control unit 34 extracts the feature of the face of the target person P captured by the overall imaging unit 38, checks the feature of the face that is extracted against the feature of a face that is registered in the database 35, and determines match/non-match based on a check score. In the case of determining that the target person P is a new person (or in other words, there is no matching feature) (Y in S32), the mode control unit 34 performs S33, and in other case (N in S32), the mode control unit 34 performs S36.

When the target person P is determined to be a new person in S32, the mode control unit 34 selects the first imaging mode (the registration mode) in S34. Then, the mode control unit 34 performs S12.

When the target person P is determined not to be a new person in S32, the mode control unit 34 selects the second imaging mode (the authentication mode) in S36. Then, the mode control unit 34 performs S12.

In this manner, according to the sixth example embodiment, the overall imaging unit 38 of the imaging system 30 entirely captures (the face of) the target person P, and the mode control unit 34 thereby determines the imaging mode. The imaging mode may thus be automatically selected, and time required for capturing may be further reduced.

Additionally, in the sixth example embodiment, the mode control unit 34 selects the first imaging mode (the registration mode) in S34 in the case of failure of face authentication. Instead, the mode control unit 34 may, in S34, cause a question asking whether the target person P is a new person to be displayed on an unspecified type of display input means (not shown) of the imaging system 30, for example, and may additionally determine whether the target person P is a new person by receiving input of an answer. Also in this case, in the case of a use where not many target persons P are newly registered, for example, rough screening may be automatically performed in relation to the imaging mode by first performing face authentication, and efficiency of capturing is increased.

Additionally, in the case where the target person P is determined to be a new person in S32, the mode control unit 34 may register, as new face information, the extracted feature of the face of the target person P in the database 35. A plurality of pieces of biometric information may thus be used for authentication, and variation of authentication method may be increased.

Furthermore, in the case where the target person P is not determined to be a new person in S32, the mode control unit 34 may update a record of the feature of the face of the target person P in the database 35 to the extracted feature of the face of the target person P. The database 35 may thus hold latest face information.

SEVENTH EXAMPLE EMBODIMENT

Next, a seventh example embodiment of the disclosure will be described with reference to FIGS. 16 and 17. The seventh example embodiment is characterized in that an imaging system 40 moves the position of the capture volume CV such that the target person P is positioned within the capture volume CV corresponding to the imaging mode. The imaging system 40 is a computer or the like that performs biometric authentication, especially iris authentication, and the imaging system 40 captures the focused region including an eye of the target person P, extracts biometric authentication information included in the image that is captured, and performs a process according to the purpose of use.

Figure 16:
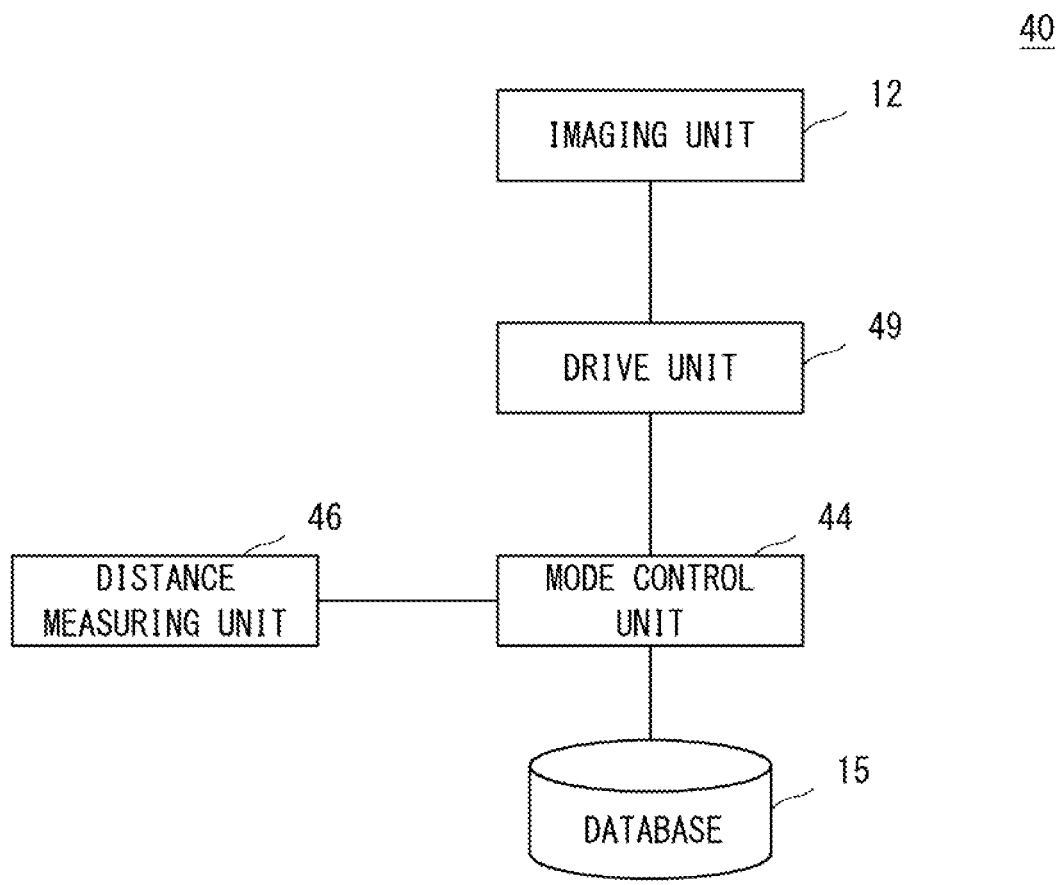
FIG. 16 is a block diagram showing a configuration of an imaging system according to a seventh example embodiment.

FIG. 16 is a block diagram showing a configuration of the imaging system 40 according to the seventh example embodiment. The imaging system 20 has structure and functions that are basically the same as those of the imaging system 10 of the second example embodiment. However, the imaging system 40 is different from the imaging system 10 in that a mode control unit 44, a distance measuring unit 46, and a drive unit 49 are included instead of the mode control unit 14.

The distance measuring unit 46 is a distance measuring sensor for measuring the position of a target person. The distance measuring unit 46 outputs a measurement result to the mode control unit 44.

The drive unit 49 is a drive unit or the like for moving the position of the capture volume CV by moving the position or orientation of the imaging unit 12 or the imaging system 40 itself.

The mode control unit 44 has structure and functions that are basically the same as those of the mode control unit 14, but in addition, the mode control unit 44 performs control of a measurement operation of the distance measuring unit 46, and control of a drive operation of the drive unit 49.

Figure 17:
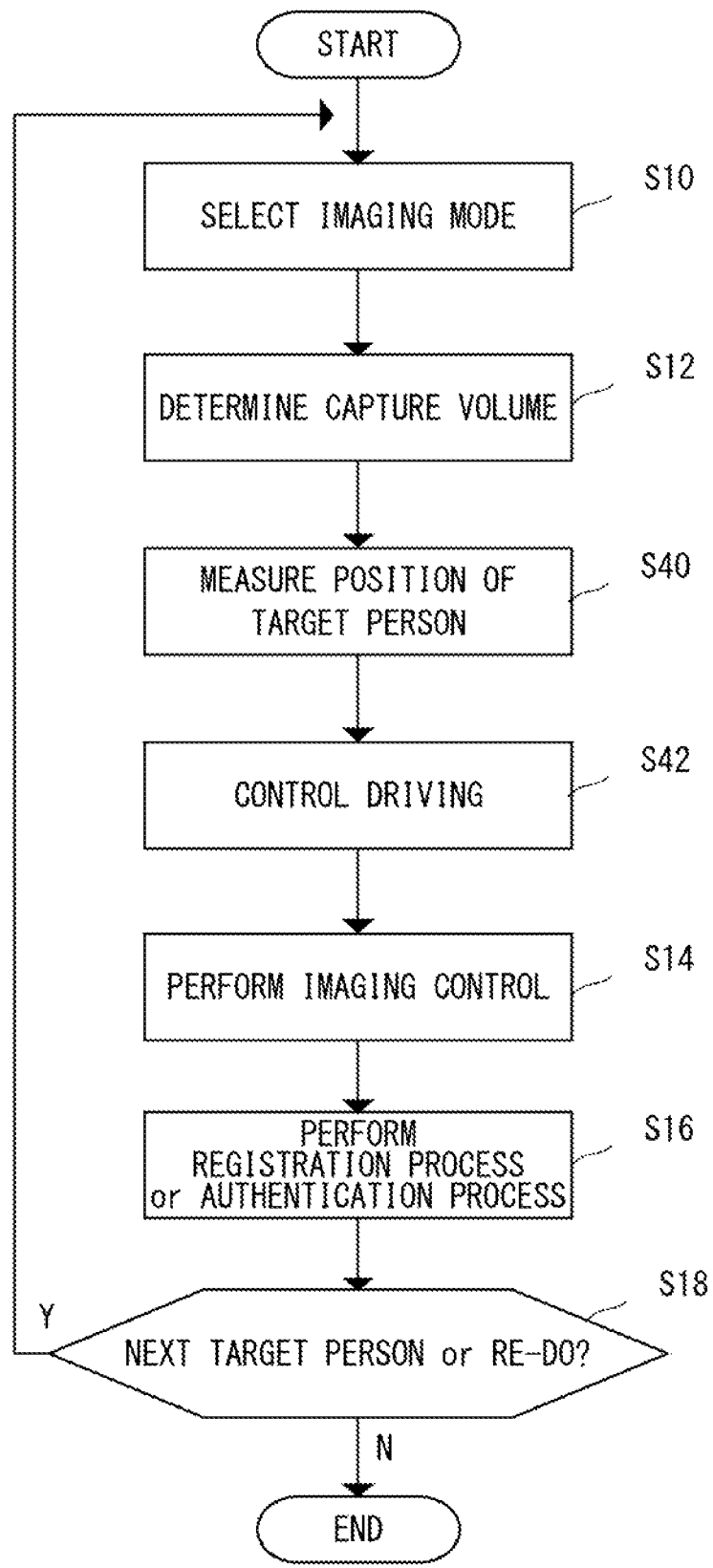
FIG. 17 is a flowchart showing a process by the imaging system according to the seventh example embodiment.

FIG. 17 is a flowchart showing a process by the imaging system 40 according to the seventh example embodiment. Steps shown in FIG. 17 include S40 to S42 in addition to the steps, shown in FIG. 4, by the imaging system 10 according to the second example embodiment. Additionally, steps the same as the steps shown in FIG. 4 will be denoted by same reference signs, and description thereof will be omitted.

In S40, in response to determination of the capture volume CV by the mode control unit 44 in S12, the distance measuring unit 46 measures the position of the target person by being controlled by the mode control unit 44. The distance measuring unit 46 outputs the position of the target person that is measured to the mode control unit 44.

In S42, the drive unit 49 moves the capture volume CV such that the target person P is positioned within the capture volume CV, by being controlled by the mode control unit 44. At this time, the drive unit 49 may change the position of the capture volume CV by moving the position of the imaging unit 12 up and down and/or forward and back. Furthermore, the drive unit 49 may change the position of the capture volume CV by changing the orientation of the imaging surface of the imaging unit 12 and swinging the optical axis left and right. Moreover, the drive unit 49 may include ground moving means such as wheels and/or air moving means such as a drone, and may move the imaging unit 12 or the imaging system 40 itself. Then, the mode control unit 44 performs S14.

In this manner, according to the seventh example embodiment, the drive unit 49 moves the position of the capture volume CV such that the target person P is positioned within the capture volume CV corresponding to the imaging mode, and thus, the target person P does not have to move at the time of capturing.

EIGHTH EXAMPLE EMBODIMENT

Heretofore, the imaging systems 10 to 40 have been described, but each of these imaging systems does not have to be a single terminal. In an eighth example embodiment, the imaging systems 10 to 40 each include a plurality of terminals different according to the imaging modes. The plurality of different terminals may be capable of communicating with a management server (not shown), the imaging system itself or the like over a network.

For example, the imaging systems 10 to 40 may each include a kiosk terminal to be used in the registration mode, and a kiosk terminal to be used in the authentication mode. The imaging system 40 may further include a mobile terminal to be used in the registration mode, including ground moving means such as wheels and/or air moving means such as a drone, and a kiosk terminal to be used in the authentication mode.

In the first to eighth example embodiments described above, the computer is a computer system including a personal computer, a word processor and the like. However, the computer may instead be a server of a local area network (LAN), a host for computer (personal computer) communication, a computer system connected to the Internet, or the like without being limited to the above. Moreover, functions may be distributed among appliances on a network, and the entire network may configure the computer.

Additionally, in the first to eighth example embodiments described above, the disclosure is described to be a configuration of hardware, but the disclosure is not limited to the same. In the disclosure, various processes such as the capturing control process, the imaging mode selection process, the registration and authentication processes, the measurement control process, the guide control process, and the overall imaging control process described above may be implemented by causing a central processing unit (CPU) to execute computer programs.

Figure 18:
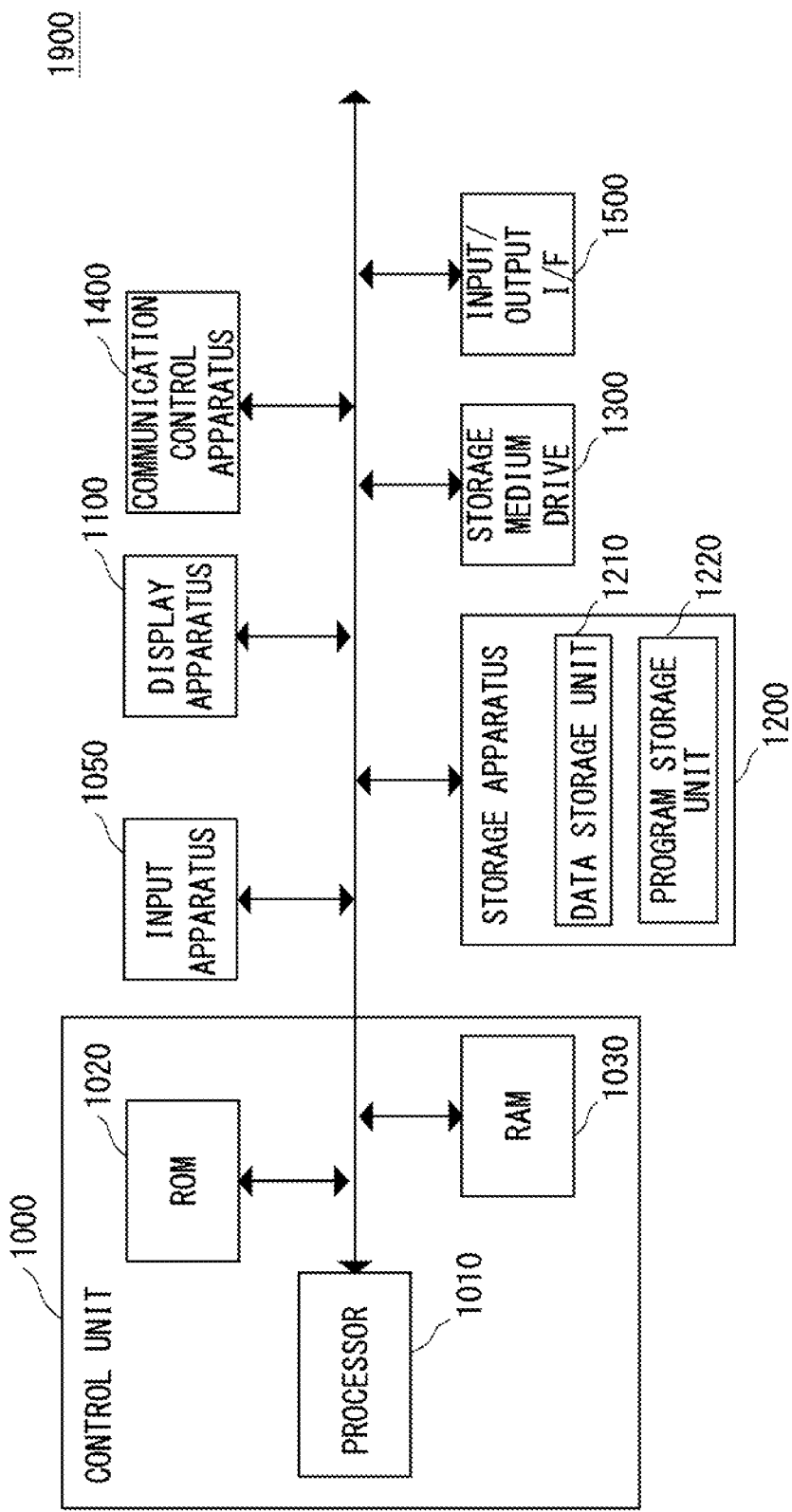
FIG. 18 is a configuration diagram of a computer according to present example embodiments.

FIG. 18 is an example of a configuration diagram of a computer 1900 according to the first to eighth example embodiments. As shown in FIG. 18, the computer 1900 includes a control unit 1000 for controlling the entire system. An input apparatus 1050, a storage apparatus 1200, a storage medium drive 1300, a communication control apparatus 1400, and an input/output I/F 1500 are connected to the control unit 1000 by a bus line such as a data bus.

The control unit 1000 includes a processor 1010, a ROM 1020, and a RAM 1030.

The processor 1010 performs various types of information processing and control according to programs stored in various storage units such as the ROM 1020 and the storage apparatus 1200.

The ROM 1020 is a read only memory in which various programs and data to be used by the processor 1010 to perform various types of control and calculation are stored.

The RAM 1030 is a random access memory that is used by the processor 1010 as a working memory. Various areas for performing various processes in the first to eighth example embodiments may be secured in the RAM 1030.

The input apparatus 1050 is an input apparatus for receiving input from a user, such as a keyboard, a mouse, and a touch panel. For example, various keys such as a numeric keypad, function keys for performing various functions, and cursor keys are arranged on the keyboard. The mouse is a pointing device, and is an input apparatus for identifying a corresponding function when a key, an icon or the like displayed on a display apparatus 1100 is clicked. The touch panel is an input appliance arranged on a surface of the display apparatus 1100, and is for identifying a touch position of a user corresponding to one of various operation keys displayed on a screen of the display apparatus 1100, and for receiving input of an operation key displayed at the touch position.

As the display apparatus 1100, a CRT or a liquid crystal display is used, for example. An input result from the keyboard or the mouse, or image information that is finally retrieved is displayed on the display apparatus. Furthermore, the display apparatus 1100 displays images of operation keys for performing various necessary operations through the touch panel, according to various functions of the computer 1900.

The storage apparatus 1200 includes a readable/writable storage medium, and a drive for reading and writing various pieces of information such as programs and data to the storage medium.

As the storage medium used in the storage apparatus 1200, a hard disk or the like is mainly used, but a non-transitory computer-readable medium used in the storage medium drive 1300 described later may alternatively be used.

The storage apparatus 1200 includes a data storage unit 1210, a program storage unit 1220, and other storage units that are not shown (such as a storage unit for backing up the programs, data and the like stored in the storage apparatus 1200). Programs for implementing various processes in the first to eighth example embodiments are stored in the program storage unit 1220. Various pieces of data in various databases according to the first to eighth example embodiments are stored in the data storage unit 1210.

The storage medium drive 1300 is a drive used by the processor 1010 to read computer programs, data including documents, and the like from a storage medium outside (an external storage medium).

The external storage medium here refers to a non-transitory computer-readable medium where computer programs, data and the like are stored. The non-transitory computer-readable medium includes various types of tangible recording media (tangible storage media). Examples of the non-transitory computer-readable media include magnetic storage media (such as flexible disks, magnetic tapes, hard disk drives, etc.), optical magnetic recording media (such as magneto-optical disks), CD-ROMs (read only memories), CD-Rs, CD-R/Ws, and semiconductor memories (such as mask ROMs, PROMs (programmable ROMs), EPROMs (erasable PROMs), flash ROMs, RAMs (random access memories), etc.). Furthermore, various programs may be supplied to a computer using various types of transitory computer-readable media. Examples of the transitory computer-readable media include electric signals, optical signals, and electromagnetic waves. The transitory computer-readable media may supply various programs to a computer via wired communication lines such as an electric wire and an optical fiber, a wireless communication line, and the storage medium drive 1300.

That is, with the computer 1900, the processor 1010 of the control unit 100 reads various programs from an external storage medium set in the storage medium drive 1300, and stores the same in respective units in the storage apparatus 1200.

In the case where the computer 1900 performs various processes, a corresponding program is read into the RAM 1030 from the storage apparatus 1200 to be executed. Alternatively, the computer 1900 may execute a program by reading the program from an external storage medium directly into the RAM 1030 by the storage medium drive 1300, instead of from the storage apparatus 1200. Furthermore, depending on the computer, various programs and the like may be stored in the ROM 1020 in advance, and be executed by the processor 1010. Moreover, the computer 1900 may download various programs and data from other storage media via the communication control apparatus 1400, and may execute the same.

The communication control apparatus 1400 is a control apparatus for networking the computer 1900 and various external electronic appliances such as other personal computers and word processors. The communication control apparatus 1400 allows the computer 1900 to be accessed from these various external electronic appliances.

The input/output I/F 1500 is an interface for connecting various input/output apparatuses via a parallel port, a serial port, a keyboard port, a mouse port and the like.

Additionally, as the processor 1010, a central processing unit (CPU), a graphics processing unit (GPU), a field-programmable gate array (FPGA), a digital signal processor (DSP), an application specific integrated circuit (ASIC), or the like may be used, or alternatively, a plurality of pieces among those listed above may be used in parallel.

An order of execution of the processes in the system and the method indicated in the claims, the specification, and the drawings may be any order as long as "before", "prior to" or the like is not clearly stated and output of a process is not used in a following process. Even when operation flows are described in the claims, the specification, and the drawings using "first," next" and the like, it does not mean that execution in this order is essential.

Heretofore, the present invention has been described with reference to the example embodiments, but the present invention is not limited by the above example embodiments. Various changes that can be understood by those skilled in the art may be made to the configuration and details of the present invention within the scope of the invention. The example embodiments described above may, but not limited to, be partially or wholly described as in Supplementary notes given below.

Supplementary Note 1

An imaging system comprising:
  an imaging unit configured to capture an eye of a target person; and
  a mode control unit configured to select one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance,
  wherein the second distance is greater than the first distance.

Supplementary Note 2

The imaging system according to Supplementary note 1, comprising a guide unit configured to guide the target person into the capture volume corresponding to the imaging mode that is selected.

Supplementary Note 3

The imaging system according to Supplementary note 1 or 2, wherein the number of pixels included in the eye that is captured in the first imaging mode is greater than the number of pixels included in the eye that is captured in the second imaging mode.

Supplementary Note 4

The imaging system according to any one of Supplementary notes 1 to 3, further comprising an overall imaging unit configured to perform capturing with a range of field of view wider than the range of field of view of the imaging unit,
  wherein the mode control unit determines the imaging mode based on an image from the overall imaging unit.

Supplementary Note 5

An imaging method comprising:
  a step of capturing an eye of a target person by an imaging unit; and
  a step of selecting, by a mode control unit, one of imaging modes including
  a first imaging mode that sets a capture volume for which a greatest distance from the imaging unit in an optical axis direction of the imaging unit is a first distance, and a second imaging mode that sets the capture volume for which the greatest distance from the imaging unit is a second distance,
  wherein the second distance is greater than the first distance.

Supplementary Note 6

A non-transitory computer-readable medium storing an imaging program for causing a computer to implement:
  an imaging function of causing an imaging unit to perform a process of capturing an eye of a target person; and
  a mode control function of selecting one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance, the second distance being greater than the first distance.

REFERENCE SIGNS LIST 1, 10, 20, 30, 40 IMAGING SYSTEM
2, 12 IMAGING UNIT
4, 14, 24, 34, 44 MODE CONTROL UNIT
15, 35 DATABASE
46 DISTANCE MEASURING UNIT
27 GUIDE UNIT
38 OVERALL IMAGING UNIT
49 DRIVE UNIT
P TARGET PERSON
CV CAPTURE VOLUME
DF FORWARD MOST DISTANCE
DB REARWARD MOST DISTANCE
DB1 FIRST DISTANCE
DB2 SECOND DISTANCE
1000 CONTROL UNIT
1010 PROCESSOR
1020 ROM
1030 RAM
1050 INPUT APPARATUS
1100 DISPLAY APPARATUS
1200 STORAGE APPARATUS

1210 DATA STORAGE UNIT
1220 PROGRAM STORAGE UNIT
1300 STORAGE MEDIUM DRIVE
1400 COMMUNICATION CONTROL APPARATUS
1500 INPUT/OUTPUT I/F
1900 COMPUTER

What is claimed is:

1. An imaging system comprising:
an imaging unit configured to capture an eye of a target person;
at least one memory storing instructions; and
at least one processor configured to execute the instructions to select one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance,
wherein the second distance is greater than the first distance.

2. The imaging system according to claim 1, wherein the at least one processor is to guide the target person into the capture volume corresponding to the imaging mode that is selected.

3. The imaging system according to claim 1, wherein the number of pixels included in the eye that is captured in the first imaging mode is greater than the number of pixels included in the eye that is captured in the second imaging mode.

4. The imaging system according to claim 1, further comprising an overall imaging unit overall imaging unit configured to perform capturing with a range of field of view wider than the range of field of view of the imaging unit,
wherein the at least one processor is to determine the imaging mode based on an image from the overall imaging unit.

5. An imaging method comprising:
capturing an eye of a target person by an imaging unit; and
selecting, one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance,
wherein the second distance is greater than the first distance.

6. A non-transitory computer-readable medium storing an imaging program for causing a computer to implement:
causing an imaging unit to perform a process of capturing an eye of a target person; and
selecting one of imaging modes including a first imaging mode that sets a capture volume for which a greatest distance from the imaging unit in an optical axis direction of the imaging unit is a first distance, and a second imaging mode that sets the capture volume for which the greatest distance from the imaging unit is a second distance, the second distance being greater than the first distance.

* * * * *